(12) United States Patent
Pedersen et al.

(10) Patent No.: US 7,214,217 B2
(45) Date of Patent: May 8, 2007

(54) OSTOMY APPLIANCE HAVING OUTER AND INNER POUCHES JOINED BY PEELABLE SEAMS AND A FILTER FOR DEODORIZING FLATUS GASES

(75) Inventors: Ole Pedersen, Frederiksberg (DK); Claudio Giori, Riverwoods, IL (US); Jørgen Forbjerg-Larsen, Skaevinge (DK)

(73) Assignee: Hollister Incorporated, Libertyville, IL (US)

( * ) Notice: Subject to any disclaimer, the term of this patent is extended or adjusted under 35 U.S.C. 154(b) by 41 days.

(21) Appl. No.: 11/018,603

(22) Filed: Dec. 21, 2004

(65) Prior Publication Data

US 2005/0143696 A1     Jun. 30, 2005

Related U.S. Application Data

(60) Provisional application No. 60/531,776, filed on Dec. 22, 2003.

(30) Foreign Application Priority Data

Dec. 22, 2003  (DK) .................... PA 2003 01912

(51) Int. Cl.
*A61F 5/441* (2006.01)
*A61F 5/448* (2006.01)

(52) U.S. Cl. ............ 604/333; 604/342; 604/338; 604/339; 604/332; 604/334; 604/335; 604/336; 604/337; 604/340; 604/341; 604/343

(58) Field of Classification Search ............ 604/342, 604/333, 338, 339, 332, 334, 335, 336, 337, 604/340, 341, 343, 344, 345
See application file for complete search history.

(56) References Cited

U.S. PATENT DOCUMENTS

| 4,232,672 A | | 11/1980 | Steer et al. |
| 4,419,100 A | * | 12/1983 | Alexander .................. 604/339 |
| 4,439,191 A | * | 3/1984 | Hogan ........................ 604/332 |
| 4,460,363 A | | 7/1984 | Steer et al. |
| 4,518,087 A | * | 5/1985 | Goglio ........................ 383/210 |
| 4,551,490 A | * | 11/1985 | Doyle et al. .................. 524/22 |
| 4,610,677 A | * | 9/1986 | Mohiuddin ................. 604/339 |
| 4,705,512 A | * | 11/1987 | Faucher ....................... 604/332 |

(Continued)

FOREIGN PATENT DOCUMENTS

EP     0 259 184     11/1991

(Continued)

OTHER PUBLICATIONS

International Serach Report, PCT/US2004/043002, dated May 18, 2005.

(Continued)

*Primary Examiner*—Tatyana Zalokaeva
*Assistant Examiner*—Paula L. Craig
(74) *Attorney, Agent, or Firm*—Marshall, Gerstein & Borun LLP (57) ABSTRACT

An ostomy appliance is provided with inner and outer pouches separably joined together by peelable seams. A vent passage and deodorizing filter are also provided, most advantageously located externally of the pouches, and a pre-filter is preferably positioned in advance of the deodorizing filter.

24 Claims, 6 Drawing Sheets

U.S. PATENT DOCUMENTS

| | | | |
|---|---|---|---|
| 4,816,027 A * | 3/1989 | Gilchrist et al. | 604/339 |
| 4,826,495 A * | 5/1989 | Petersen | 604/333 |
| 4,986,824 A * | 1/1991 | Steer et al. | 604/333 |
| 5,209,744 A * | 5/1993 | Abe et al. | 604/342 |
| 5,306,264 A * | 4/1994 | Ferguson et al. | 604/333 |
| 5,417,678 A * | 5/1995 | Baumann et al. | 604/333 |
| 5,423,782 A | 6/1995 | Wolrich | |
| 5,591,144 A * | 1/1997 | Smith et al. | 604/327 |
| 5,674,578 A * | 10/1997 | Giori | 428/35.4 |
| 5,690,622 A * | 11/1997 | Smith et al. | 604/333 |
| 5,722,965 A * | 3/1998 | Kuczynski | 604/344 |
| 5,769,831 A * | 6/1998 | Freeman et al. | 604/332 |
| 5,785,695 A * | 7/1998 | Sato et al. | 604/339 |
| 5,865,819 A * | 2/1999 | Cisko et al. | 604/339 |
| 5,938,647 A | 8/1999 | Smith | |
| 5,989,235 A * | 11/1999 | Quacquarella et al. | 604/332 |
| 6,033,758 A * | 3/2000 | Kocher et al. | 428/138 |
| 6,135,986 A * | 10/2000 | Leisner et al. | 604/322 |
| 6,506,184 B1 * | 1/2003 | Villefrance | 604/333 |
| 6,902,551 B2 * | 6/2005 | Hansen et al. | 604/342 |
| 2002/0088080 A1 * | 7/2002 | Fenton | 15/389 |
| 2003/0023210 A1 * | 1/2003 | Bedard et al. | 604/332 |
| 2004/0059306 A1 * | 3/2004 | Tsal et al. | 604/332 |

FOREIGN PATENT DOCUMENTS

| | | |
|---|---|---|
| GB | 2348141 A * | 9/2000 |
| WO | WO 94/12128 | 6/1994 |

OTHER PUBLICATIONS

Written Opinion, PCT/US2004/043002, dated May 18, 2005.

* cited by examiner

OSTOMY APPLIANCE HAVING OUTER AND INNER POUCHES JOINED BY PEELABLE SEAMS AND A FILTER FOR DEODORIZING FLATUS GASES

CROSS REFERENCE TO RELATED APPLICATIONS

This application claims priority from U.S. Provisional Application Ser. No. 60/531,776, filed Dec. 22, 2003, and Danish Application No. 2003/01912, filed Dec. 22, 2003, as to all subject matter commonly disclosed therein.

FIELD OF THE INVENTION

The present invention relates to an ostomy appliance for receiving discharge from a human stoma and comprising:
attachment means for attaching the appliance to the peristomal skin surface of a user of the appliance, and
an ostomy pouch assembly comprising:
an inner pouch attached to said attachment means and having a first aperture for receiving the stoma of said user,
said inner pouch being defined by a flexible body side or proximal inner pouch wall and a flexible distal inner pouch wall, and one or more peripherally extending inner pouch sealing seams,
an outer pouch enclosing said inner pouch, attached to said attachment means and having a second aperture for receiving said stoma and being aligned with said first aperture,
said outer pouch being defined by a flexible body side or proximal outer pouch wall and a flexible distal outer pouch wall, and one or more peripherally extending outer pouch sealing seams,
said one or more outer pouch sealing seams being manually peelable such that the attachment forces provided by said one or more peelable outer pouch sealing seams may be manually eliminated by manually pulling said distal outer pouch wall in a direction transverse to said one or more peelable outer pouch sealing seams.

SUMMARY OF THE INVENTION

An ostomy appliance of the type indicated is disclosed in co-pending and co-owned International Patent Application No. PCT/U.S. 2004/034759, the disclosure of which is hereby incorporated herein by reference.

Venting of flatus gas from the pouch assembly is normally necessary to avoid ballooning, and it is important that the gas venting means be such that gas venting is carried out efficiently and in such a manner that the odor of the flatus gas is eliminated to the highest possible degree.

In the ostomy appliance according to the invention, the attachment means comprise an adhesive face plate for securing said ostomy pouches to the skin of an ostomy patient, the faceplate comprising:
a flexible plate with a bodyside or proximal surface and a distal surface and comprising a layer of a skin friendly adhesive material and a stoma receiving aperture for receiving a stoma of said patient, and
generally annular face plate coupling means having an inner and an outer periphery and attached to said face plate and adapted for fixedly or releasably engaging corresponding generally annular pouch coupling means attached to said ostomy pouch, the face plate coupling means being secured to said flexible plate with the plane of said face plate coupling means generally parallel to the plane of said flexible plate and generally concentric with said aperture for receiving said stoma,
one or more filters for deodorising flatus gas, and
one or more flatus gas passages extending from the area located within said inner periphery and through said deodorising filter.

Hereby, an efficient gas venting and deodorising arrangement is achieved. A further advantage is obtained in the case of two-piece ostomy appliances where the pouch assembly is replaced several times when full. The relatively expensive deodorising filter is used during the entire wear time of the face plate, and thus the cost of replacing the filter together with the pouch assembly is eliminated, also allowing use of a more efficient and consequently more expensive deodorising filter.

Although the deodorising filter and flatus gas passages may be arranged in many different manners on or in the faceplate, for instance with the filter arranged in a compartment provided in the body of the faceplate coupling means or in a compartment in attached to said coupling means, in the currently preferred embodiment of the ostomy appliance according to the invention, the one or more flatus gas passages extend in the region between said face plate coupling means and said flexible plate from said inner periphery to said outer periphery and through said filter.

Advantageously, the face plate may further comprise a compartment having an exterior portion located outside said outer periphery and an interior portion located between said coupling ring and said flexible plate, a flatus gas outlet being provided in a wall of said exterior portion, said compartment forming part of said flatus gas passage, said filter being located within said compartment such that said flatus gas outlet is obstructed by said filter.

In the currently preferred embodiment of an ostomy appliance according to the invention, the face plate further comprises a venting bag made of a film of plastic material and extending outward beyond said outer periphery, said film being provided with a flatus gas outlet aperture, said flatus gas passage extending from said inner periphery into the interior of said venting bag and through both said filter and said flatus gas outlet aperture, said filter being located entirely in said venting bag and such that substantially all said flatus gas vented through said flatus gas aperture flows through said filter.

Hereby, a particularly inexpensive solution is achieved that is easy to produce with the equipment utilized to produce the pouch assembly and face plate.

In the currently preferred embodiment of an ostomy appliance according to the invention, the assembly furthermore comprises an elongate, preferably closed loop obstructing or pre-filter means attached to said inner pouch along the edge of said first aperture and extending through said second aperture in said outer pouch, and the pre-filter means comprises a ring of a gas permeable material such as open cell foam or non-woven material that preferably is biodegradable and/or hydrophobic, and furthermore the pre-filter means is arranged in the vicinity of or adjacent to said inner periphery such that substantially all said flatus gas vented through said flatus gas aperture flows through said pre-filter means.

Hereby, it is achieved that the deodorising filter is not clogged by stomal liquids or solids, because the pre-filter only allows flatus gas to pass through to the filter in any appreciable amounts. Furthermore, the pre-filter prevents stomal liquids and solids from soiling the face plate and pouch coupling means so that the pouch coupling means may be disposed of without having to take into consideration such soiling.

In the currently preferred embodiment of an ostomy appliance according to the invention, said one or more outer pouch sealing seams peelably attach said distal outer pouch wall to said distal inner pouch wall and said proximal outer pouch wall to said proximal inner pouch wall.

Alternatively or additionally, said one or more outer pouch sealing seams may peelably attach said distal outer pouch wall directly to said proximal outer pouch wall.

In the currently preferred embodiment of an ostomy appliance according to the invention, the material of said inner pouch walls is biodegradable, and preferably the inner pouch walls are made of a plastic film laminated to a web of a non-woven fibrous material, preferably cellulosic material such as paper, preferably a paper of a toilet tissue type, said web facing outwards relative to the interior of said inner pouch, the non-woven material preferably being biodegradable.

In the currently preferred embodiment of an ostomy appliance according to the invention, the inner pouch walls are impermeable to liquid and gas and preferably permeable to odors, and the outer pouch walls are impermeable to liquid, gas and odors.

In the currently preferred embodiment of an ostomy appliance according to the invention, the proximal inner pouch wall is attached to the proximal outer pouch wall in a region surrounding said first and second apertures by means of a peelable interior sealing seam.

In the currently preferred embodiment of an ostomy appliance according to the invention, the appliance either being a two-piece appliance or a one-piece appliance, the face plate coupling means and said pouch coupling means are mutually matching coupling rings adapted for releasably engaging one another.

In the currently preferred embodiment of an ostomy appliance according to the invention, the pre-filter means is attached to an annular film which in turn is attached to said inner pouch along said edge of said first aperture.

DETAILED DESCRIPTION OF THE SEVERAL VIEWS OF THE DRAWINGS

In the following, the invention will be explained more in detail with reference to various embodiments of the invention shown, solely by way of example, in the drawings, where.

DETAILED DESCRIPTION OF THE PREFERRED EMBODIMENTS

Referring now to FIGS. 1–6 an ostomy appliance referenced generally by the numeral 1 comprises an outer pouch 2 having a body side or proximal wall 2a and an opposed distal wall 2b. The appliance furthermore comprises an inner pouch 3 having a proximal wall 3a and a distal wall 3b. The outer pouch walls 2a and 2b are covered by a comfort layer 4 of a non-woven material.

Figure 1:
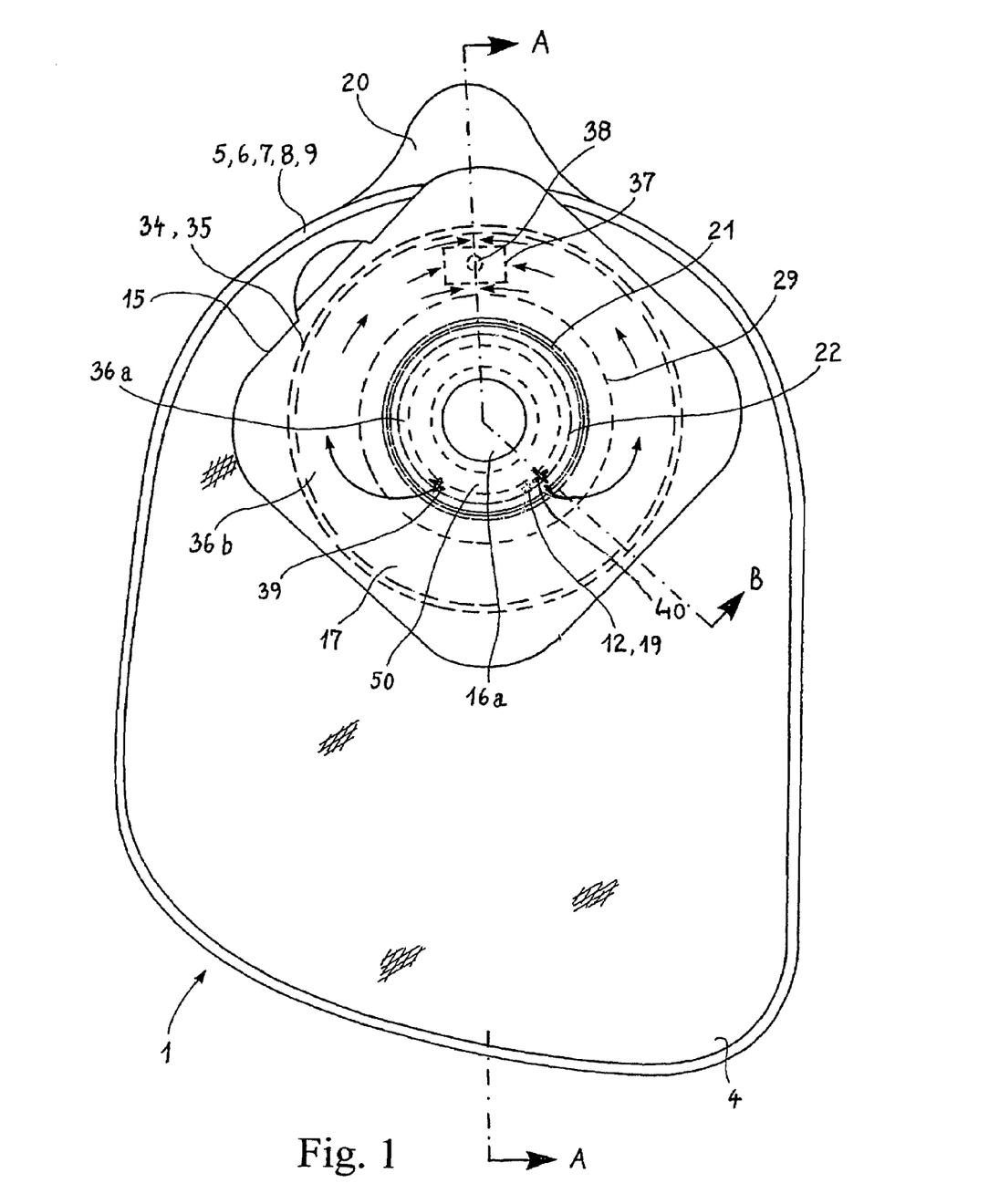
FIG. 1 is a schematic plan view, seen from the body side, of a first embodiment of a two-piece ostomy pouch according to the invention with an inner pouch arranged inside an outer pouch and with a face plate provided with a deodorising filter.
Figure 2:
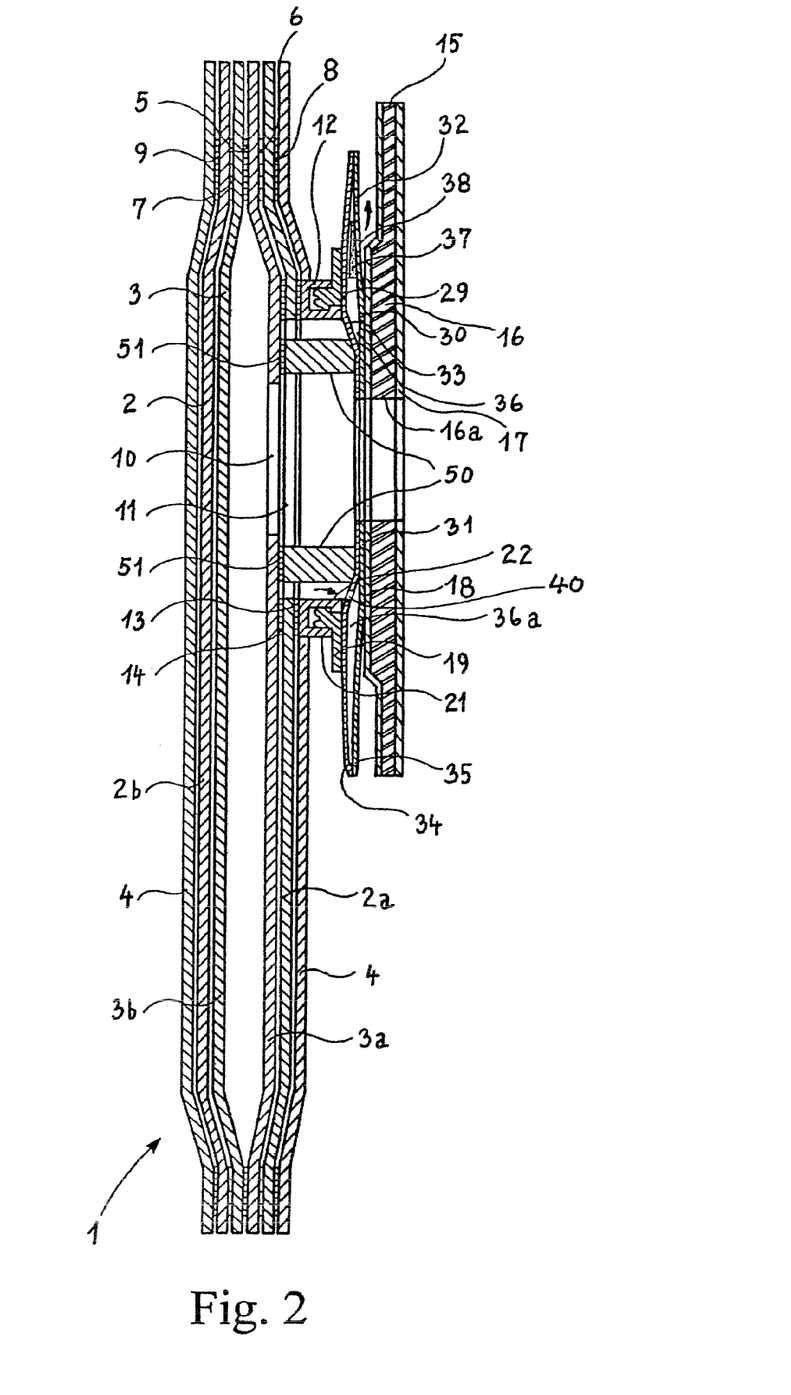
FIG. 2 is a diagrammatic cross sectional view taken along line A—A of the pouches in FIG. 1 and along line A–B of the face plate in FIG. 1 with the film thicknesses exaggerated for illustrative purposes.
Figure 3:
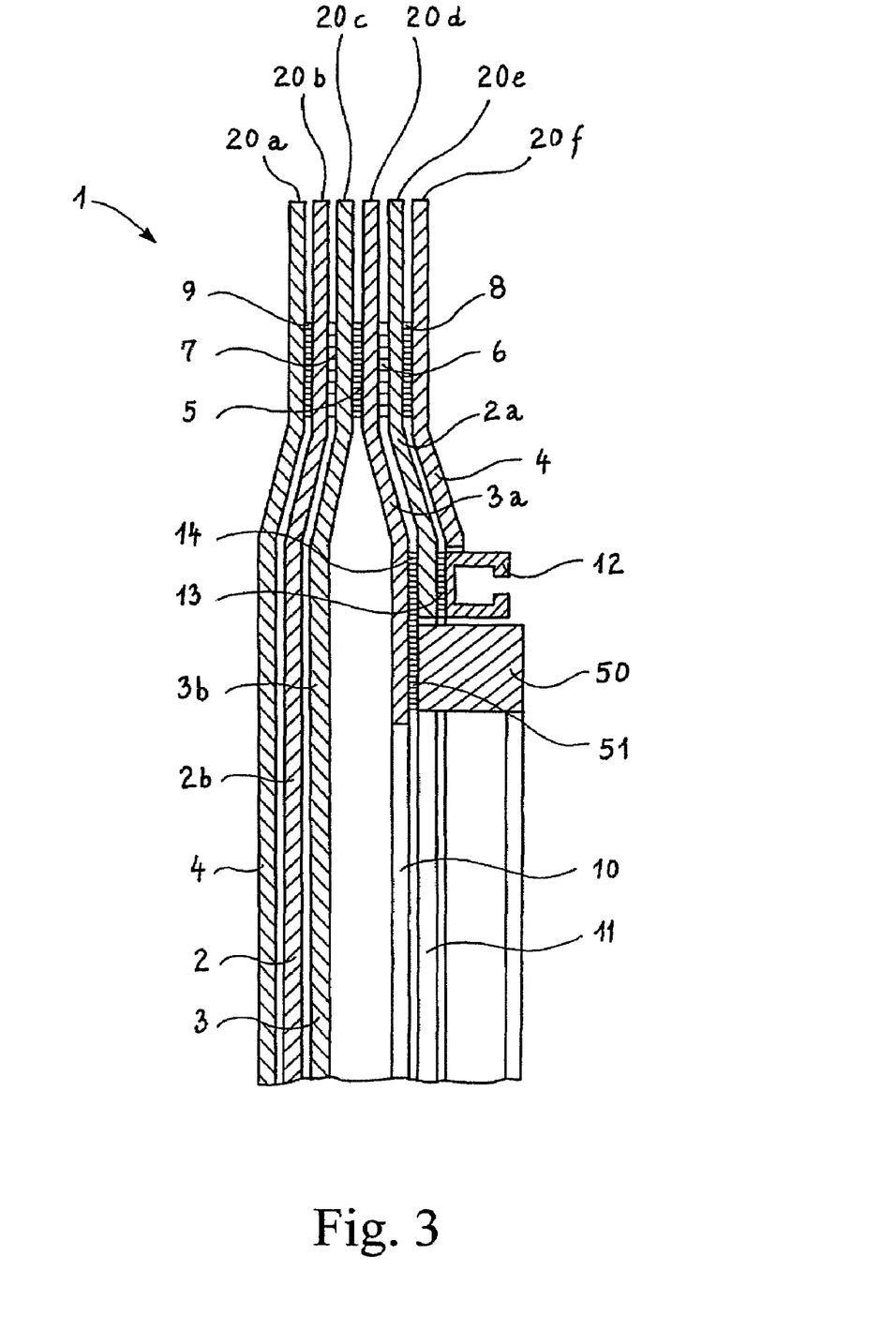
FIG. 3 is an enlarged scale view of the top portion of the pouch assembly of FIG. 2.

The walls 2a and 2b of the outer pouch are made of a flexible plastic film that is impermeable to liquids, gases and odors. The walls 3a and 3b of the inner pouch are made of a flexible plastic film that is impermeable to liquids and gases and permeable to odors.

The inner pouch 3 is formed by sealingly securing the two inner walls 3a and 3b to each other along the peripheries thereof by means of an inner pouch seam 5 either being a heat sealing seam (e.g. a RF seam) or an adhesive seam.

The outer pouch 2 is formed by sealing the proximal and distal outer pouch walls 2a and 2b, respectively, to the inner pouch proximal and distal walls 3a and 3b, respectively by means of peelable sealing seams 6 and 7, respectively, extending along the outer periphery of the outer and inner pouch walls.

The comfort layers 4, which are optional, are sealed to the outer pouch walls 3a and 3b by means of heat sealing (e.g. RF sealing) or adhesive seams 8 and 9, respectively, extending along the outer periphery of the outer pouch walls.

Both the inner pouch 3 and the outer pouch 2 have a stoma receiving aperture 10 and 11, respectively in the proximal walls 3a and 2a, respectively.

The appliance 1 further comprises a pouch coupling ring 12 secured to the proximal outer pouch wall 2a by means of a circumferential heat seal 13 or other suitable means. The area surrounding the aperture 10 of the proximal inner pouch wall 3a is attached to the corresponding area of the proximal outer pouch wall 2a by means of an annular peelable seam 14.

The appliance 1 further comprises a face plate assembly 15 (not shown in FIGS. 3–5) having an adhesive layer 16 for adhering the face plate assembly to the peristomal surface of a user of the appliance 1 after having removed a release sheet 17 covering the proximal or body side surface of the adhesive layer 16. The adhesive layer is provided with a stoma receiving aperture 16a.

Figure 6:
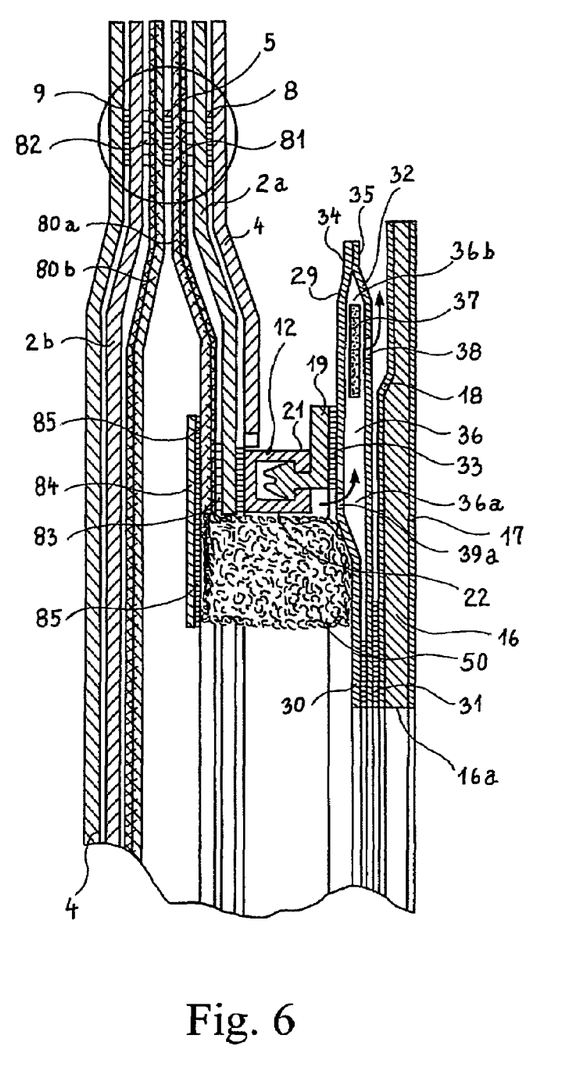
FIG. 6 is a an enlarged scale view of the top portion of the currently preferred embodiment of an ostomy appliance according to the invention with an inner pouch arranged inside an outer pouch and with a face plate provided with a deodorising filter.

A carrier sheet 18 is attached to the distal surface of the adhesive layer 16, and a face plate coupling ring 19 is secured to the carrier sheet 18, such that interconnection of the two coupling rings 12 and 19 as shown in FIGS. 2 and 6 will allow the pouch assembly 2, 3 to be adhered to the peristomal skin surface of a user with the stoma inserted in the apertures 16a, 10 and 11 such that stomal discharge may enter the inner pouch 3.

The inner and outer walls 2a, 2b, 3a, 3b as well as the comfort layers 4 project outwardly and upwardly and are prolonged at the top of the appliance to form a tongue or projection 20 for providing non-connected and separable gripping tabs 20a–20f for the separation of the two pouches by peeling the peelable seams 6 and 7 for separate disposal of the two pouches, the inner (soiled) pouch in a toilet and the outer (unsoiled) pouch in a pocket or hand bag.

In use, when the inner pouch is full of stomal discharge and the pouch needs to be replaced by an empty pouch, the user or a helper grips the tabs 20a and 20b together with one hand and the rest of the tabs 20c–20f with the other hand and pulls the tabs 20a and 20b away from the body and downwardly. Hereby the connection between the outer pouch wall 2b and the inner pouch wall 3b by means of the peelable sealing seam 7 is broken or disrupted (peeled) such that the proximal outer pouch wall 2b with its comfort layer 4 is peeled away from the appliance 1.

Thereafter, the user grips the tabs 20c and 20d together with one hand and the tabs 20e and 20f with the other hand and pulls the tabs 20c and 20d outwardly and downwardly whereby the peelable sealing seam 6 gives way (peels) so that the inner pouch 3 is peeled away from the outer pouch proximal wall 2a until the level of the top point of the peelable sealing seam 14 is reached. This peelable seam 14 also gives way to the pulling force exerted on the tabs 20c and 20d so that finally the entire inner pouch 3 with its content of stomal discharge has been peeled away from the proximal outer pouch wall 2a. The stoma of the user is now exposed.

Now the inner pouch 3 with contents can be deposited in the bowl of a toilet and flushed away while the proximal outer pouch wall 2a with comfort layer 4 and coupling ring 13 can be removed from the face plate assembly 15. The outer pouch walls 2a and 2b with corresponding comfort layers 4 and the coupling ring can now be folded together and be disposed of in some other manner, for instance in a pocket, a hand bag or a refuse container as they are not soiled by coming into contact with stomal liquids or solids.

The adhesive layer 16 may be formed of any suitable pressure-sensitive adhesive commonly used for securing the faceplates of ostomy appliances to the peristomal skin surfaces of a wearer. For example, a hypoallergenic medical-grade acrylic adhesive may be used. However, it is preferable that the adhesive layer be formed of a soft, skinfriendly hydrocolloid-containing adhesive material that is capable of absorbing moisture and has both wet and dry tack. Such a material is commonly referred to as a skin barrier composition and typically comprises a continuous elastomeric adhesive phase having hydrocolloid particles dispersed throughout the continuous phase. Initial tack, usually referred to as "dry tack," is provided by the continuous phase but, because such a composition is occlusive or non-breathable, adherence to the skin would be disrupted by perspiration and by liquid stomal discharge if it were not for the dispersed hydrocolloids which absorb fluids and thereby maintain and possibly enhance adhesive attachment to the skin. U.S. Pat. No. 4,551,490 and other references disclose that suitable water-absorbing and swellable hydrocolloid gums may include sodium carboxymethylcellulose, pectin, gelatine, guar gum, locust bean gum, and the like. The elastomers used in the continuous phase may be polyisobutylene, natural rubber, silicone rubber, acrylonitrile rubber and other elastomers known in the art to have similar properties.

Referring now to FIGS. 1–2 and 6, a silicone treated release sheet 17 of plastic material is applied to the body side or proximal surface of the adhesive layer 16 for protecting the adhesive layer 16 until the faceplate is to be applied to the skin of a wearer thereof.

A carrier sheet 18 of heat sealable plastic material is attached to the distal surface of the adhesive layer 16. An aperture 16a for receiving a stoma of a wearer of the face plate is provided in the layer 16 and in the sheets 17 and 18.

A coupling ring 12 of a flexible plastic material and having an outer periphery 21 and an inner periphery 22 is adapted for engaging the corresponding coupling ring 19 of the face plate 15 for securing the pouch to the wearer such that stomal material may be collected in the pouch 3 when the faceplate 1 with the pouches 2 and 3 secured to the faceplate is adhered to the peristomal skin of the wearer.

The coupling ring 19 is secured to the adhesive layer 16 by means of a first annular strip 29 of film of a heat sealable plastic material having one edge 30 attached by heat sealing to one edge 31 of a second annular strip 32 of film of a heat sealable plastic material which edge 31 in turn is attached to the carrier sheet 18 by heat sealing. The coupling ring 19 is attached to the film strip 29 at 33 by heat sealing whereby the coupling ring 19 is flexibly attached to the adhesive layer 16.

Edges 34 and 35 of the strips 29 and 32, respectively, opposed to the edges 30 and 31, respectively, are heat sealed to one another such that an annular compartment or chamber 36 is formed having an interior portion 36a located in the region between the coupling ring 19 and the adhesive layer 16 and an exterior portion 36b in the form of a venting pouch or bag located outside the exterior periphery 21 of the coupling ring 12. The film strips 29 and 32 may be integral such that the heat sealing of edges 34 and 35 may be avoided.

A flatus gas deodorising filter 37 is arranged in the exterior portion 36b of the compartment 36 and is adhered to film strip 32 such that it covers a flatus gas outlet aperture 38 provided in film strip 32.

In the FIGS. 1–2 embodiment, two spaced flatus gas inlet apertures 39 and 40 are provided in the portion of the film strip 29 located inside the inner periphery 22 of the coupling ring 12. The inlet apertures 39 and 40 are located remote from the outlet gas aperture 38. The inlet apertures 39 and 40 are made by cutting a cross-shaped incision in the film strip 29.

Many more apertures may be provided along the annular extent of the film strip 29. Thus, in the FIG. 6 embodiment, a series of flatus gas inlet apertures 39a are provided in the portion of the film strip 29 located inside the inner periphery 22 of the coupling ring 12 evenly distributed along the circumference of the film strip 29.

The apertures 39, 39a or 40 for leading the flatus gas from the stoma received in the aperture 16a to the filter 37 may become clogged and thereby obstructed by solid and liquid stomal effluents.

Therefore, an obstruction means for solids and liquids in the form of a closed loop configured structure, preferably, and as shown in FIGS. 1–4 and 6, a ring 50 of gas permeable material such as resilient open cell foam material or nonwoven, preferably a biodegradable material, but also usefully of any other resilient or also semi-rigid or rigid material allowing flatus gases to pass therethrough, but hinder or prevent stomal effluent solids and liquids from passing therethrough, is arranged between the aperture 16a and the coupling rings 12, 19 to allow flatus gases to pass through the obstruction means into the chamber 36 and through the filter 37 and out of the aperture 38, but hinder solids and liquids to pass through into the chamber 36 such that the filter 37 is not clogged by said solids and liquids.

The currently preferred material for the ring 50 is fibers of 100% rayon coated with a paraffin wax (a paraffin emulsion Aurapel 374 supplied by the company Bayer Chemie). The ring has a thickness of approx. 9 mm and a weight of 38 oz/sqy and is supplied by the company National Nonwoven.

The surface of the ring 50 facing the stoma receiving aperture 16*a* may be treated with a skin friendly product such as aloe vera or some other porous skin friendly cream such that any contact between the ring and the stoma will bring the skin friendly material into contact with the stoma.

In the FIGS. 1–4 embodiments the ring 50 is attached to the inner pouch wall 3*a* around the aperture 10 by means of an annular seam 51 of adhesive or heat sealing such that the ring 50 is removed together with the inner pouch 3 and flushed through a toilet.

The axial extent of the ring 50 is slightly larger than the distance between the inner pouch wall 3*a* and the carrier sheet 18 when the coupling rings 12 and 19 are engaged such that in said engaged position of the coupling rings the ring 50 is slightly axially compressed such that a pressure is exerted by the ring 50 on the strip 29 and carrier sheet 18 to ensure that no solids and liquids may pass between the ring 50 and the face plate 15.

In use, the release sheet 17 is removed from the adhesive layer 16, and the proximal surface of the layer 16 is applied to the peristomal skin of a wearer such that the stoma is received in the aperture 16*a*. The collecting ostomy pouches 2 and 3 then attached to the faceplate 15 by engaging the coupling ring 12 of the pouches with the matching coupling ring 19.

Stomal material consisting of solid material, liquid and flatus gas is then discharged from the stoma into the inner pouch 3. The solid material and liquid falls down into the inner pouch 3 while the flatus gas is led out through the ring 50 and the flatus gas passages defined by the inlet apertures 39 and 40, the interior compartment portion 36*a* and the exterior compartment portion 36*b*, the filter 37 and the flatus gas outlet 38. The flow of the flatus gas is indicated by means of arrows.

The filter 37 is of the type disclosed in U.S. Pat. No. 6,506,184 hereby incorporated herein by reference. However, any other suitable type of deodorising filter may be used.

The coupling ring 12 is flexibly attached to the flexible plate 15 with the advantages inherent in this design as explained and disclosed in co-owned U.S. Pat. Nos. 4,419, 100 and 5,730,735 hereby incorporated herein by reference.

When the inner pouch 3 is full and is to be substituted by an empty pouch, the inner and outer pouches are peeled apart as described above and the coupling rings 12 and 19 are disengaged so that a new set of inner and outer pouches with a new, clean ring 50 are attached to the face plate 15.

Hereby a new pre-filter ring 50, unsoiled by stomal solids and liquids is provided such that the flatus gas again can flow unhindered by any solids and liquids adhered to the inner surface of the ring 50 to the filter 37.

Furthermore, the ring 50 prevents stomal solids and liquids from soiling the coupling ring 12 of the outer pouch 2 so that it can be folded together with the outer pouch distal and proximal walls 2*a* and 2*b* and disposed of in a pocket or bag as described above without emitting any odors.

The ring 50 also prevents stomal solids and liquid from contacting the coupling ring 19 of the face plate 15 as well as a major region of the distal surface of the face plate 15 located between the coupling ring 19 and the stoma receiving aperture 16*a*. This renders the cleaning of the face plate when replacing the pouches 2 and 3 much easier and more effective as only the region between the inner surface of the ring 50 and the stoma received in the aperture 16*a* is to be cleaned.

The material of the ring 50 may be any suitable porous, preferably at least slightly resilient, material such as foam, non-woven material, textile, gauze and so on.

Figure 4:
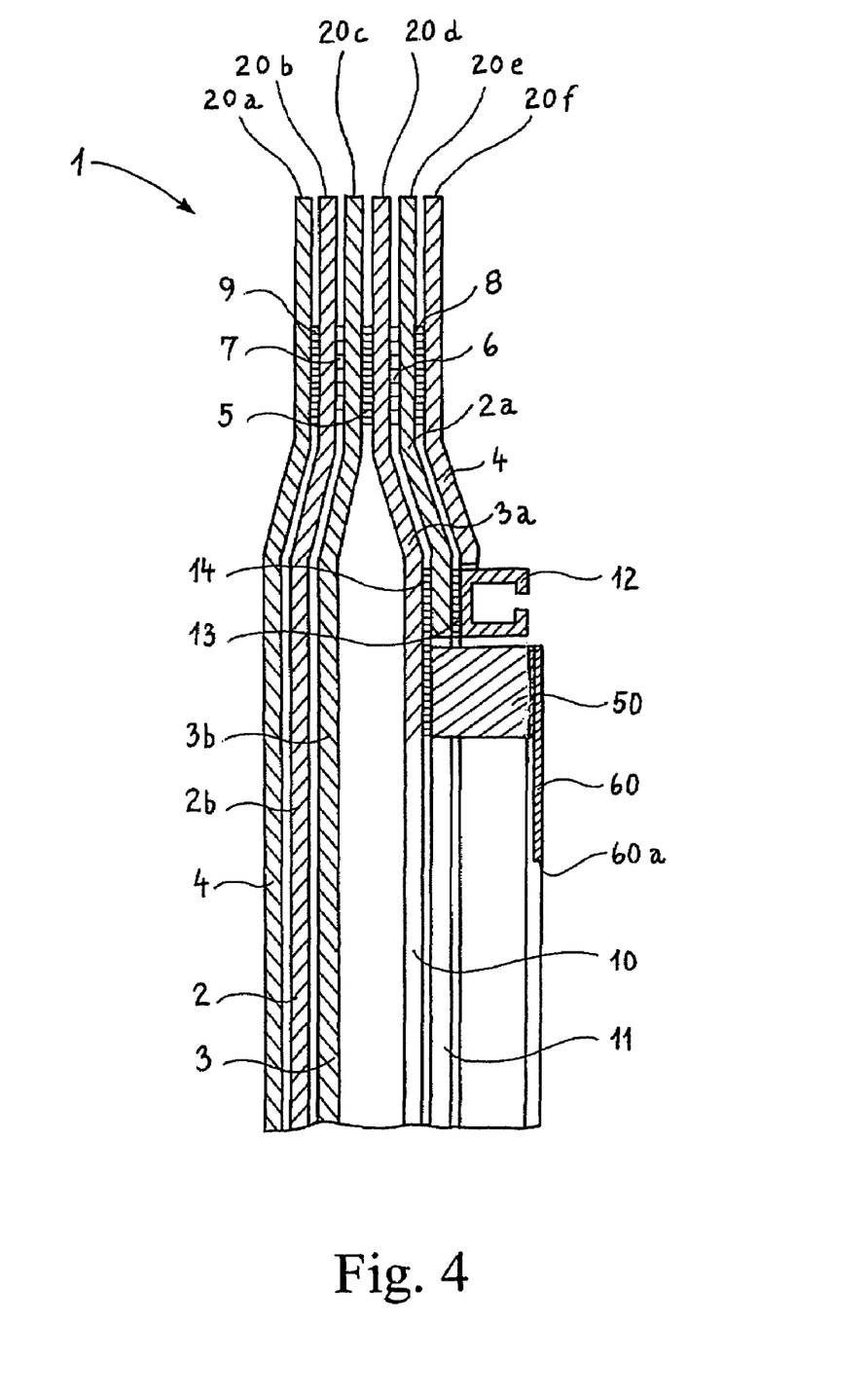
FIG. 4 is a view as FIG. 3 of an alternative embodiment.

Referring now to FIG. 4, the obstructing or pre-filter ring 50 is provided with an annular film 60 attached to the proximal surface of the ring 60 and extending from the outer surface of the ring 50 to an aperture 60*a* coinciding with the not shown aperture 16*a* of the face plate 15.

When the pouch 3 is removed, the ring 50 and annular film will "sweep" any stomal material lodged between the ring 50 and the stoma away such that the entire distal surface of the face plate between the coupling ring 12 and the stoma aperture 16*a* is clean.

The obstructing means may be a ring of plastic or cardboard or other suitable material attached at the distal edge region thereof to the inner pouch 3 or the outer pouch 2 or the coupling ring 19 and provided at the proximal edge region thereof with a flexible annular apron resiliently contacting the distal surface of the face plate between the coupling ring 12 and the stoma aperture 16*a*.

Figure 5:
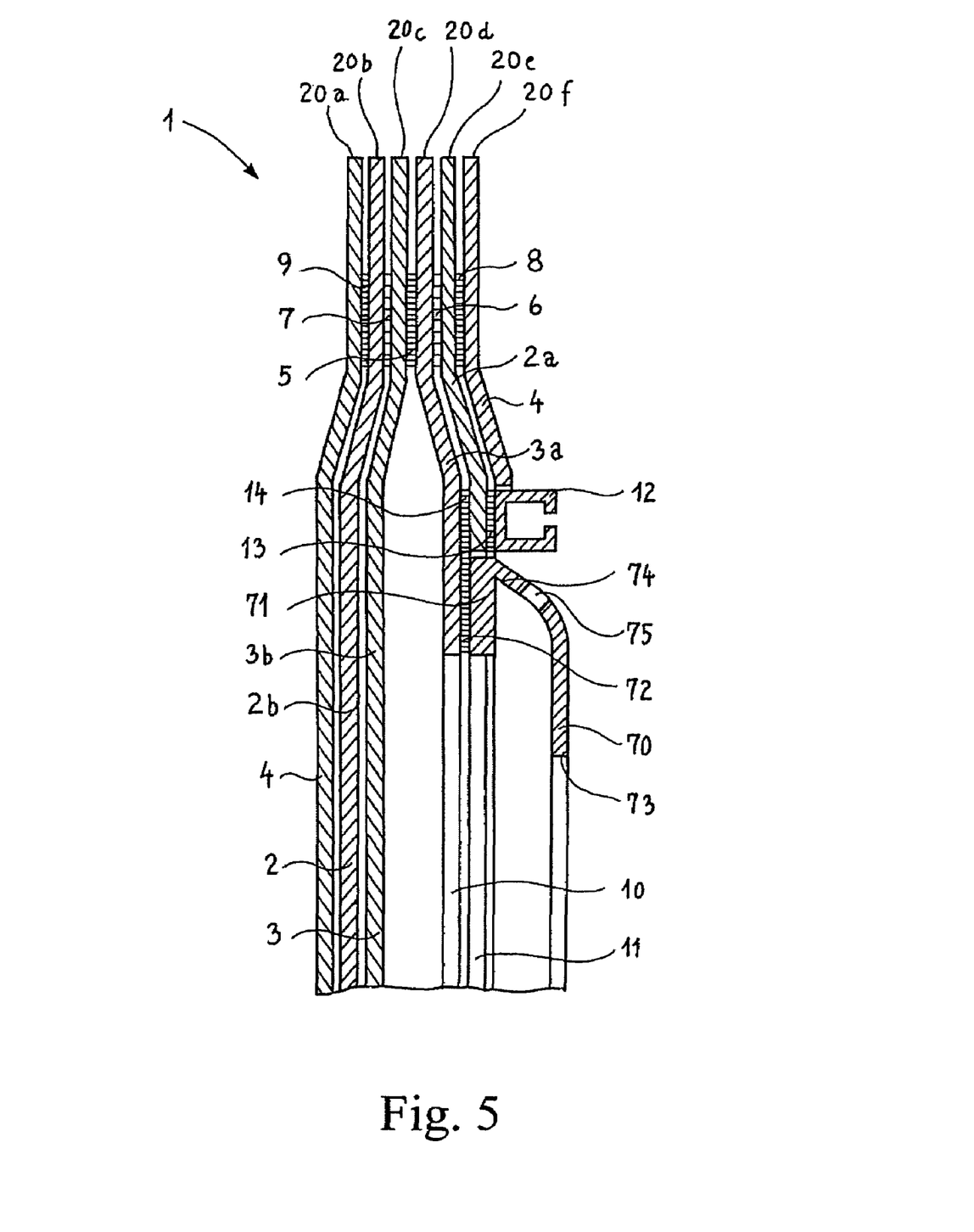
FIG. 5 is a view as FIGS. 3 and 4 of a further alternative embodiment.

An example of such a ring is shown in FIG. 5, where such a ring 70 of resilient plastic, preferably biodegradable, material has a body portion 71 thereof attached to the proximal inner pouch wall 3*a* around the aperture 10 thereof by means of an adhesive seam or weld 72. A resilient apron 73 intended for pressing resiliently against the not shown carrier sheet 18 is attached to the body portion by means of an intermediate portion 74.

The ring 70 functions in the same manner as the ring 60 in FIG. 4.

If the intermediate portion 74 is provided with a great number of flatus gas apertures as shown at 75 and preferably with a diameter of approx. 0.5 mm and distributed around the entire circumference of the intermediate portion, the ring will also function as a flatus gas pre-filter much as ring 50 in FIGS. 1–4 and 6.

The ring 50 may be configured such that the inner surface facing the stoma is inclined such that the proximal surface of the ring contacting the face plate is radially wider than the distal surface, preferably such that the inner rim of said proximal surface is adjacent the rim of the stoma receiving aperture of the face plate such that the ring 50 may perform the "wiping" or "sweeping" function described above when the pouch or pouches are removed.

Generally speaking, the material of the inner and outer pouch walls may be a film of any suitable plastic material. The outer pouch wall film material is impermeable to liquids, gases and odors, while the inner pouch wall film is impermeable to liquids and gases, but not necessarily to odors.

It is preferable that the inner pouch wall film material be biodegradable so that the sewage treatment facilities are not inconvenienced to an unnecessary degree. By allowing the inner pouch wall film to be permeable to odors, the film may be made thinner and thus be more easily disintegrated and biodegraded.

Examples of biodegradable films suitable for the inner pouch walls 3*a* and 3*b* are biodegradable aliphatic polyesters such as polycaptrolactone.

Biodegradable and liquid impermeable materials that currently are considered suitable for the inner pouch wall film are biodegradable aliphatic polyesters such as polycaprolactone (for instance TONE Polymer supplied by Dow Chemical Company) or a biodegradable aliphatic-aromatic copolyester (for instance ECOFLEX supplied by BASF). Suitable inner pouch wall materials are disclosed in co-pending and co-owned International Patent Application No. PCT/US 2004/034760, the disclosure of which is hereby incorporated herein by reference.

The peelable sealing seams 6, 7 and 14 may be provided in various ways, for instance by utilizing a peel lacquer or varnish which gives a peelable adhesion to either the inner or the outer pouch walls or to both walls. The type of peelable lacquer or varnish depends on the material chosen for the pouch bag films.

Peel lacquers that currently are considered to be suitable for certain film materials are "Appeel" resins from the company duPont, and hot melt peelable adhesives supplied under the trade names Dispomelt 34-2881, 34-5519, Instaweld 34–3306 and Bondmaster 34-3306 by the companies National Starch Adhesive and Chemical Corporation.

Another way of implementing the peelable sealing seams is to use an intermediate film of polybutylene or an intermediate three-layer film supplied by the company Rexam under the trade name Core-Seal, the peeling occurring between the two outer films and the internal film or layer, the external films being securely heat sealed to the inner and outer pouch wall films.

A further way of implementing the peelable seams is to use a silicone release film such as the type used for labels.

In the context of the present invention, the term peelable utilized in the specification and claims is to be understood to mean that the connection between two films, be it by means of an adhesive, heat sealing or other means, can be broken, disrupted or eliminated by manually urging one film away from the other without compromising the integrity of the films.

Figure 7:
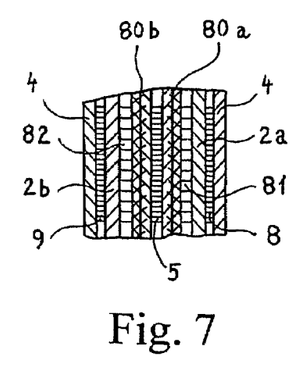
FIG. 7 is an even more enlarged scale view of the encircled region of FIG. 6.

A currently preferred manner of providing peelable sealing seams will now be described with reference to FIGS. 6–7. The embodiment of FIGS. 6–7 is identical to the embodiment of FIGS. 1–2 except for the inner pouch bag walls 80a and 80b that are made of a heat sealable, liquid and gas impermeable, odor permeable film of plastic material laminated to a web of cullulosic fiber, for instance tissue paper.

The paper sheet (indicated by cross hatches) is located on the outer surface of the inner pouch walls 80a and 80b facing the outer pouch walls 2a and 2b, respectively.

The peelable sealing seams 81, 82 and 83 between the inner pouch walls 80a, 80b and the outer pouch walls 2a, 2b, respectively are provided by heat sealing whereby the plastic material of the outer pouch walls 2a and 2b melts and flows into the interstices of the paper sheet such that a bond is created between the films 2a and 2b and the paper sheet.

However, as the plastic material does not flow all the way through the paper sheet to fuse with the plastic material of the inner pouch walls 80a and 80b, respectively, the strength of the bond created by the heat sealing is dependent on the internal adherence forces between the fibers of the paper sheet and/or between the fibers and the films 2a, 2b and 80a, 80b.

By applying a peeling force transversely to the surface of the paper sheet, the bond can be broken manually so that the walls 2a and 80a and 2b and 80b can be separated by the manual peeling action described above for separating the outer pouch walls from the inner pouch for toilet disposal of the latter.

Alternatively, the outer pouch walls may be peelably adhered to the paper sheet by means of an adhesive having greater adhesion strength than the inner cohesion of the paper fibers. Finally, it is conceivable that the peelability of the seams be obtained by a relatively weak adhesion between, on the one hand, the outer pouch walls and/or the inner pouch walls and, on the other hand, the paper sheet so that the inner cohesion of the paper fibers is of less importance.

In the FIG. 6 embodiment the ring 50 is attached to the inner pouch wall 80a by means of an annular film 84 to which the ring 50 is attached by a seam 85 of adhesive or heat sealing. The film ring 84 is attached to the inner pouch wall 80a by means of a seam 85 of adhesive or heat sealing. Hereby, a much more secure attachment of the pre-filter ring 50 to the inner pouch wall 80a is achieved than if the ring 50 were attached to the paper covered surface of the inner pouch wall 80a.

Although all the embodiments shown and described are of the two-piece type having mechanical coupling means for attaching the pouch assembly to the face plate, a two-piece ostomy appliance according to the invention may be provided with coupling means of the type where a releasable adhesive is applied to a bodyside or proximal annular coupling surface on the pouch assembly for releasably adhering the pouch assembly to a corresponding distal annular surface of the face plate.

A one-piece ostomy appliance according to the invention may be provided with annular coupling means for fixedly attaching the pouch assembly to the faceplate, for instance an annular seam of adhesive or of heat sealing.

We claim:

1. An ostomy appliance for receiving discharge from a human stoma and comprising:
   attachment means for attaching the appliance to the peristomal skin surface of a user of the appliance, and
   an ostomy pouch assembly comprising
   an inner pouch attached to said attachment means and having a first aperture for receiving the stoma of said user,
   said inner pouch being defined by a flexible body side or proximal inner pouch wall and a flexible distal inner pouch wall, and one or more peripherally extending inner pouch sealing seams,
   an outer pouch enclosing said inner pouch, attached to said attachment means and having a second aperture for receiving said stoma and being aligned with said first aperture,
   said outer pouch being defined by a flexible body side or proximal outer pouch wall and a flexible distal outer pouch wall, and one or more peripherally extending outer pouch sealing seams,
   said one or more outer pouch sealing seams being manually peelable such that the attachment forces provided by said one or more peelable outer pouch sealing seams may be manually eliminated by manually pulling said distal outer pouch wall in a direction transverse to said one or more peelable outer pouch sealing seams, said attachment means comprising
   an adhesive face plate for securing said inner and outer pouches to the skin of an ostomy patient, said faceplate comprising:
   a flexible plate with a bodyside or proximal surface and a distal surface and comprising a layer of a skin friendly adhesive material and a stoma receiving aperture for receiving a stoma of said patient, and
   generally annular face plate coupling means having an inner and an outer periphery and attached to said face plate and adapted for fixedly or releasably engaging corresponding generally annular pouch coupling means attached to said inner and outer pouches, the face plate coupling means being secured to said flexible plate with the plane of said face plate coupling means generally parallel to the plane of said flexible plate and generally concentric with said aperture for receiving said stoma, one or more filters for deodorising flatus gas, and one or more flatus gas passages extending from the area located within said inner periphery and through said deodorising filter.

2. An ostomy appliance according to claim 1, wherein said one or more flatus gas passages extend in the region between said face plate coupling means and said flexible plate from said inner periphery to said outer periphery and through said filter.

3. An ostomy appliance according to claims 1 or 2, wherein said face plate further comprises a compartment having an exterior portion located outside said outer periphery and an interior portion located between said coupling ring and said flexible plate, a flatus gas outlet being provided in a wall of said exterior portion, said compartment forming part of said flatus gas passage, said filter being located within said compartment such that said flatus gas outlet is obstructed by said filter.

4. An ostomy appliance according to claims 1 or 2, wherein said face plate further comprises a venting bag made of a film of plastic material and extending outward beyond said outer periphery, said film being provided with a flatus gas outlet aperture, said flatus gas passage extending from said inner periphery into the interior of said venting bag and through both said filter and said flatus gas outlet aperture, said filter being located entirely in said venting bag and such that substantially all said flatus gas vented through said flatus gas aperture flows through said filter.

5. An ostomy appliance according to claims 1 or 2, wherein said assembly furthermore comprises an elongate, closed loop obstructing or pre-filter means attached to said inner pouch along an edge of said first aperture and extending through said second aperture in said outer pouch.

6. An ostomy appliance according to claim 5, wherein said pre-filter means comprises a ring of a gas permeable material which is biodegradable and/or hydrophobic.

7. An ostomy appliance according to claim 6 wherein said gas permeable material is open cell foam or non-woven material.

8. An ostomy appliance according to claim 5, wherein said pre-filter means is arranged in the vicinity of or adjacent to said inner periphery such that substantially all said flatus gas vented through said flatus gas aperture flows through said pre-filter means.

9. An ostomy appliance according to claim 5, wherein said pre-filter means is attached to an annular film which in turn is attached to said inner pouch along said edge of said first aperture.

10. An ostomy appliance according to claims 1 or 2, wherein said one or more outer pouch sealing seams peelably attach said distal outer pouch wall to said distal inner pouch wall and said proximal outer pouch wall to said proximal inner pouch wall.

11. An ostomy appliance according to claim 10, wherein said one or more outer pouch sealing seams peelably attach said distal outer pouch wall directly to said proximal outer pouch wall.

12. An ostomy appliance according to claim 10, wherein said inner pouch walls are made of a plastic film laminated to a web of a non-woven fibrous material, said web facing outwards relative to the interior of said inner pouch.

13. An ostomy appliance according to claim 12, wherein said nonwoven material and/or said plastic film are biodegradable.

14. An ostomy appliance according to claim 12 in which said non-woven fibrous material is paper of a toilet tissue type.

15. An ostomy appliance according to claim 10 wherein said proximal inner pouch wall is attached to said proximal outer pouch wall in a region surrounding said first and second apertures by means of a peelable interior sealing seam.

16. An ostomy appliance according to claim 1 or 2 wherein said inner pouch walls are impermeable to liquid and gas, and said outer pouch walls are impermeable to liquid, gas and odors.

17. An ostomy appliance according to claims 1 or 2, wherein said face plate coupling means and said pouch coupling means are mutually matching coupling rings adapted for releasably engaging one another.

18. An ostomy appliance for receiving discharge from a human stoma and comprising:

attachment means for attaching the appliance to the peristomal skin surface of a user of the appliance, and an ostomy pouch assembly comprising:

an inner pouch attached to said attachment means and having a first aperture for receiving the stoma of said user, said inner pouch being defined by a flexible body side or proximal inner pouch wall and a flexible distal inner pouch wall, and one or more peripherally extending inner pouch sealing seams, an outer pouch enclosing said inner pouch, attached to said attachment means and having a second aperture for receiving said stoma and being aligned with said first aperture, said outer pouch being defined by a flexible body side or proximal outer pouch wall and a flexible distal outer pouch wall, and one or more peripherally extending outer pouch sealing seams, said one or more outer pouch sealing seams being manually peelable such that the attachment forces provided by said one or more peelable outer pouch sealing seams may be manually eliminated by manually pulling said distal outer pouch wall in a direction transverse to said one or more peelable outer pouch sealing seams, said attachment means comprising:

an adhesive face plate for securing said inner and outer pouches to the skin of an ostomy patient, said faceplate comprising:

a flexible plate with a bodyside or proximal surface and a distal surface and comprising a layer of a skin friendly adhesive material and a stoma receiving aperture for receiving a stoma of said patient, and generally annular face plate coupling means having an inner and an outer periphery and attached to said face plate and adapted for fixedly or releasably engaging corresponding generally annular pouch coupling means attached to said inner and outer pouches, the face plate coupling means being secured to said flexible plate with the plane of said face plate coupling means generally parallel to the plane of said flexible plate and generally concentric with said aperture for receiving said stoma, one or more filters for deodorising flatus gas, one or more flatus gas passages extending from the area located within said inner periphery and through said deodorising filter, and an elongate, closed loop pro-filter means attached to said inner pouch along an edge of said first aperture and extending through said second aperture in said outer pouch, said one or more outer pouch sealing scams peelably attaching said distal outer pouch wall to said distal inner pouch wall and said proximal outer pouch wall to said proximal inner pouch wall.

19. An ostomy appliance according to claim 18, wherein said pre-filter means comprises a ring of a gas permeable open cell foam or non-woven material which is biodegradable and/or hydrophobic.

20. An ostomy appliance according to claim 19, wherein said pre-filter means is arranged in the vicinity of or adjacent to said inner periphery such that substantially all said flatus gas vented through said flatus gas aperture flows through said pre-filter means.

21. An ostomy appliance according to claim 18, wherein said inner pouch walls are made of a plastic film laminated to a web of a non-woven fibrous material, said web facing outwards relative to the interior of said pouch.

22. An ostomy appliance according to claim 21 wherein said non-woven fibrous material is paper of a toilet tissue type.

23. An ostomy appliance according to claim 18, wherein said inner pouch walls are impermeable to liquid and gas, and said outer pouch walls are impermeable to liquid, gas and odors.

24. An ostomy appliance according to claim 18, wherein said proximal inner pouch wall is attached to said proximal outer pouch wall in a region surrounding said first and second apertures by means of a peelable interior sealing seam.

* * * * *